(12) United States Patent
Fuimaono et al.

(10) Patent No.: US 10,350,007 B2
(45) Date of Patent: *Jul. 16, 2019

(54) CATHETER ADAPTED FOR USE WITH GUIDE WIRE FOR ACCESSING VESSELS

(71) Applicant: Biosense Webster (Israel) Ltd., Yokneam (IL)

(72) Inventors: Kristine B. Fuimaono, Costa Mesa, CA (US); Debby Esther Grunewald, Los Angeles, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/853,638

(22) Filed: Dec. 22, 2017

(65) Prior Publication Data

US 2018/0116716 A1 May 3, 2018

Related U.S. Application Data

(63) Continuation of application No. 13/840,278, filed on Mar. 15, 2013, now Pat. No. 9,848,948.

(51) Int. Cl.
*A61B 18/14* (2006.01)
*A61M 25/01* (2006.01)
*A61B 18/00* (2006.01)

(52) U.S. Cl.
CPC ..... *A61B 18/1492* (2013.01); *A61M 25/0158* (2013.01); *A61B 2018/00029* (2013.01);
(Continued)

(58) Field of Classification Search
CPC ... A61M 25/00; A61M 25/0043; A61B 18/08; A61B 18/1492; A61B 2018/0016;
(Continued)

(56) References Cited

U.S. PATENT DOCUMENTS 4,394,866 A 7/1983 Hughes
5,772,693 A 6/1998 Brownlee
(Continued)

FOREIGN PATENT DOCUMENTS

EP 1 256 326 A1 11/2002
EP 2 540 245 A1 1/2013
(Continued)

OTHER PUBLICATIONS

Extended European Search Report for EP Patent Application No. 14160376.1 dated by the EPO on Jul. 14, 2014, 6 pages.
(Continued)

*Primary Examiner* — Rex R Holmes
(74) *Attorney, Agent, or Firm* — Lewis Roca Rothgerber Christie LLP

(57) ABSTRACT

An ablation catheter adapted for use with a guide wire has a 3-D shaped portion that carries ring electrodes for ablating a vessel or tubular region, including the renal artery. The 3-D shaped portion, for example, a helical portion, enables the ring electrodes to contact an inner surface of the vessel at a plurality of locations at different depths along the vessel to form a conduction block without forming a closed conduction loop which would otherwise increase the risk of stenosis of the vessel. In one embodiment, the catheter has a lumen with entry and exit ports to allow the guide wire to pass through the lumen but bypass the 3-D shaped portion. In another embodiment, the catheter has outer bands providing side tunnels through which the guide wire can pass through.

20 Claims, 8 Drawing Sheets

(52) U.S. Cl.
CPC ........... *A61B 2018/00404* (2013.01); *A61B 2018/00434* (2013.01); *A61B 2018/00511* (2013.01); *A61B 2018/1467* (2013.01)

(58) Field of Classification Search
CPC ........ A61B 2018/00214; A61B 2018/00267; A61B 2018/00273; A61B 2018/00351; A61B 2018/00577; A61B 2018/1467
See application file for complete search history.

(56) References Cited

U.S. PATENT DOCUMENTS

| | | | |
|---|---|---|---|
| 5,997,526 A | 12/1999 | Giba et al. | |
| 6,301,507 B1 | 10/2001 | Bakels et al. | |
| 6,542,781 B1* | 4/2003 | Koblish | A61B 18/1492 607/122 |
| 6,604,283 B1 | 8/2003 | Kuzma | |
| 6,745,080 B2 | 6/2004 | Koblish | |
| 7,474,909 B2 | 1/2009 | Phan et al. | |
| 2004/0082948 A1 | 4/2004 | Stewart et al. | |
| 2005/0107819 A1 | 5/2005 | Sater | |
| 2007/0265609 A1 | 11/2007 | Thapliyal | |
| 2012/0029509 A1 | 2/2012 | Smith | |
| 2012/0143293 A1* | 6/2012 | Mauch | A61B 18/1492 607/99 |

FOREIGN PATENT DOCUMENTS

| | | |
|---|---|---|
| JP | 2003514605 | 4/2003 |
| JP | 2009536870 A | 10/2009 |
| WO | WO0137723 A2 | 5/2001 |

OTHER PUBLICATIONS

Japanese Patent Office action dated Oct. 29, 2017 in JP Application No. 2014-051094, with English translation, 7 pages.

* cited by examiner

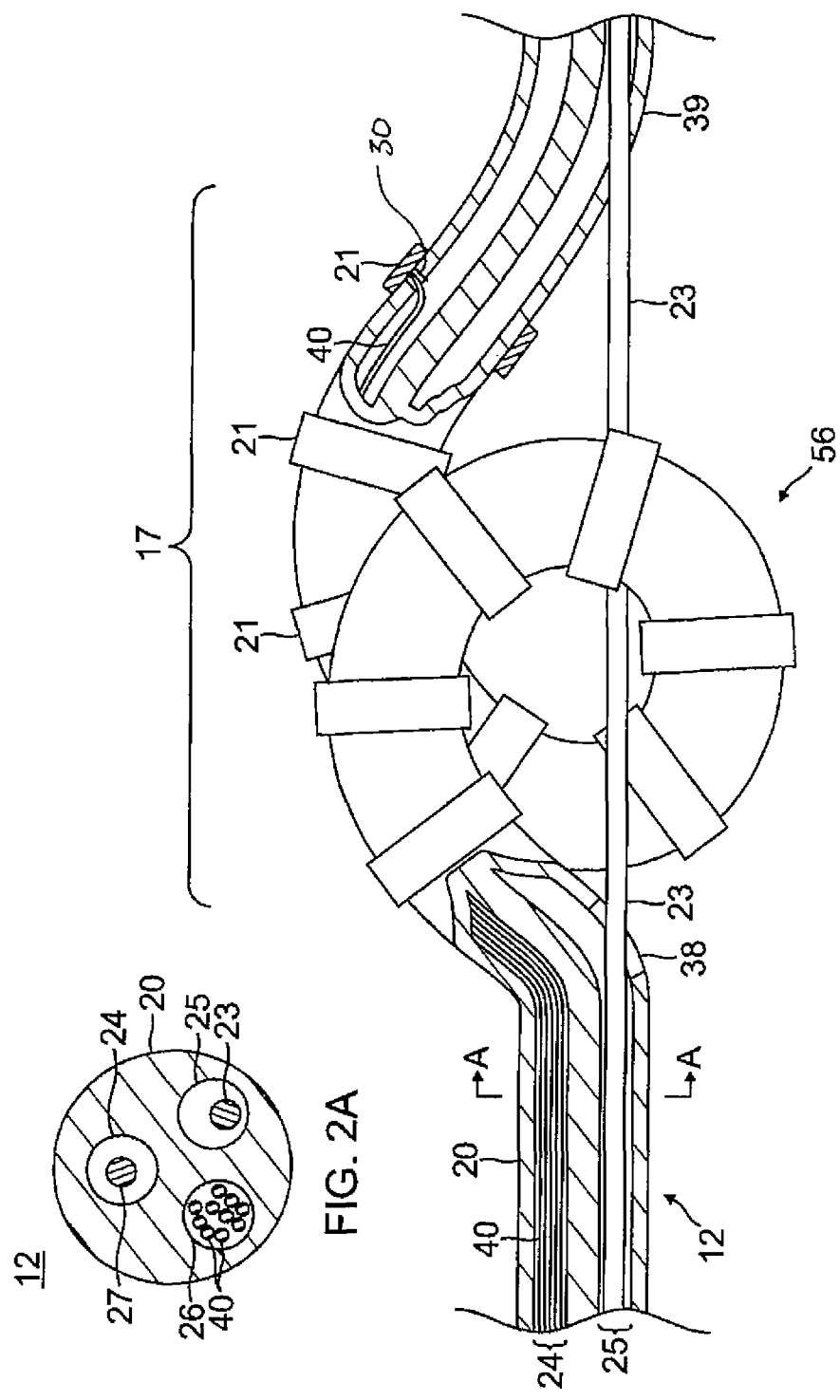

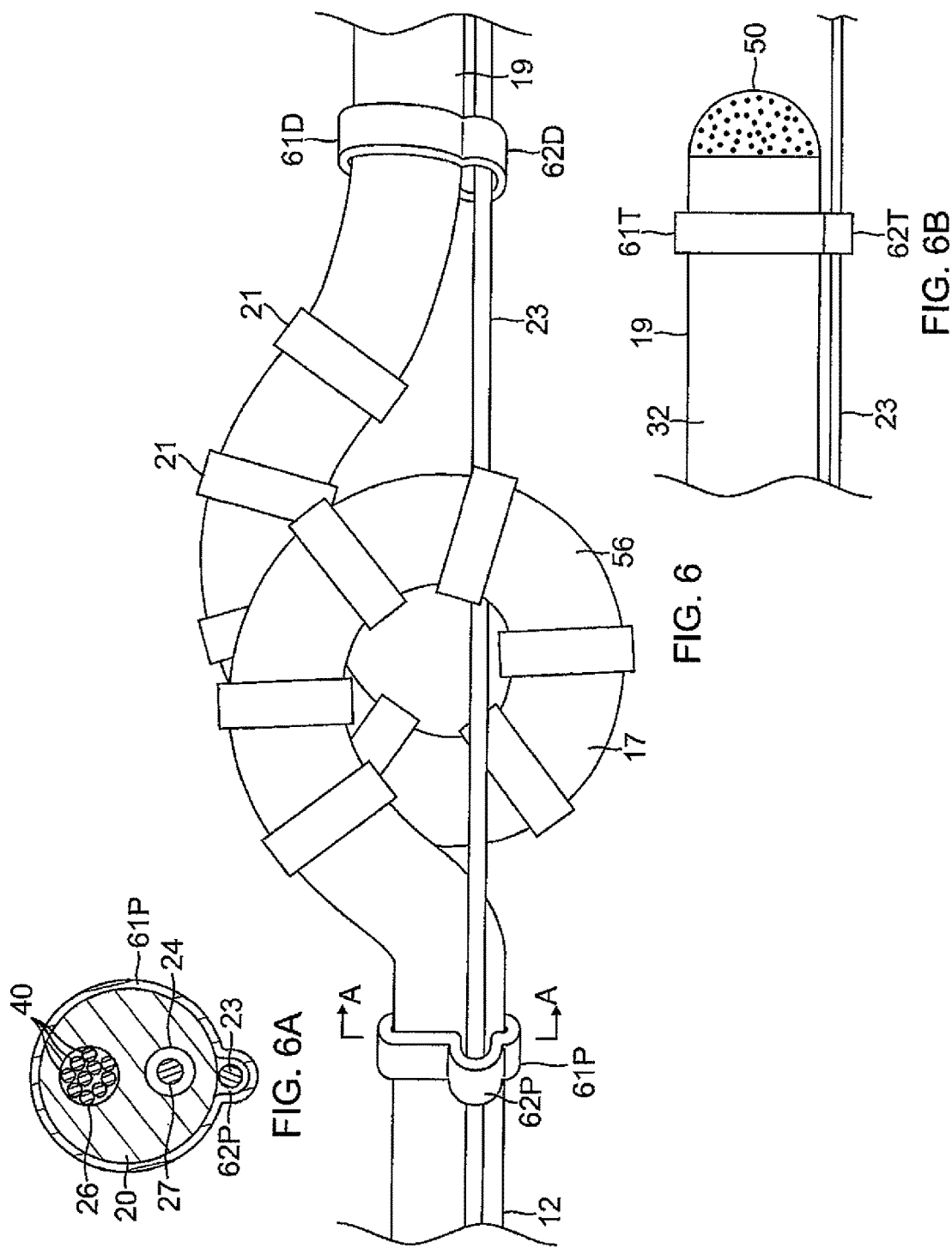

CATHETER ADAPTED FOR USE WITH GUIDE WIRE FOR ACCESSING VESSELS

CROSS-REFERENCE TO RELATED APPLICATION(S)

The present application is a continuation of and claims priority to and the benefit of U.S. application Ser. No. 13/840,278 filed Mar. 13, 2013, now U.S. Pat. No. 9,848,948, the entire content of which is incorporated herein by reference.

FIELD OF INVENTION

The present invention relates to a catheter adapted for use with a guide wire for accessing vessels or tubular regions in a patient's body. In particular, the catheter has a 3-D shape that can be straightened before entering a vessel or a tubular region.

BACKGROUND OF INVENTION

Catheterization is used in diagnostic and therapeutic procedures. For example, a cardiac catheter is used for mapping and ablation in the heart to treat a variety of cardiac ailments, including cardiac arrhythmias, such as atrial flutter and atrial fibrillation which persist as common and dangerous medical ailments, especially in the aging population. Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Another catheterization procedure is renal denervation (RDN). It is a minimally invasive, endovascular catheter based procedure using radiofrequency ablation aimed at treating hypertension. The sympathetic system fuels the release of certain hormones that affect and control blood pressure. In hypertension, the continued release of low-dose amounts of these hormones can increase blood pressure. Hypertension can be controlled by diet, exercise and drugs. However, resistant hypertension (commonly defined as blood pressure that remains above goal in spite of concurrent use of three antihypertensive agents of different classes) requires more aggressive treatments, including surgery. Resistant hypertension is a common clinical problem faced by both primary care clinicians and specialists. As older age and obesity are two of the strongest risk factors for uncontrolled hypertension, the incidence of resistant hypertension will likely increase as the population becomes more elderly and heavier.

It has been established that severing the renal nerves improves blood pressure. However, this procedure involves surgery and all its attendant risks, and often resulted in global sympathetic denervation below the chest. Being able to de-nervate, or silence, only the renal nerves through a catheter-based system is a crucial development. A small catheter is placed in the femoral artery and access to the nerves is gained through the renal artery. The nerves are embedded in the casings or layers around the renal arteries. By passing an energy source into the renal artery and transmitting a low-dose energy, radiofrequency ablation, through the catheter, inbound and exiting renal sympathetic nerves are impaired or "denerved" at selected locations along their lengths. This causes reduction of renal sympathetic afferent and efferent activity and blood pressure can be decreased.

In both cardiac ablation and renal ablation, ablation along a closed inner circumference or a narrow band in a vessel or tubular region can lead to stenosis, including narrowing, tightening or stiffening of the vessel or tubular region. Accordingly, catheters with different 3-D designs have been employed to form conduction blocks that trace open patterns, such as a helical pattern, that can block radial paths of conduction without forming a closed ring within the vessel. However, such 3-D designs typically require a supporting wire to hold the 3-D shape, and a contracting mechanism or a dedicated lumen for the guide wire for straightening the catheter entering and advancing in the patient's body, all of which undesirably increases the outer diameter of the catheter. With an increased outer diameter, use of the catheter can be significantly limited.

Accordingly, there is a desire for a catheter having a collapsible 3-D shape that can be used with a guide wire without an increase in the outer diameter of the catheter, or at least in the portion of the catheter having the 3-D shape.

SUMMARY OF THE INVENTION

The present invention is directed to an ablation catheter adapted for use with a guide wire. The catheter has a 3-D shaped portion that carries ring electrodes for ablating a vessel or tubular region, including the renal artery. The 3-D shaped portion, for example, a helical portion, enables the ring electrodes to contact an inner circumferential surface of the vessel at a plurality of radial locations at different depths along the vessel to form a conduction block without forming a closed conduction loop which would otherwise increase the risk of stenosis of the vessel.

The catheter of the presenting invention adapted for use with a guide wire, includes an elongated tubular member having a proximal portion, a distal tip section, and a 3-D shaped portion carrying ring electrodes between the proximal portion and the distal tip section, wherein the proximal portion and the distal tip section are each in longitudinal alignment with the guide wire except for the 3-D shaped portion which extends around the guide wire. The 3-D shaped portion has shape memory which allows it to collapse or deform when subjected to external forces and to reassume its predetermined shape with removal of the external forces. The shape memory allows the 3-D shaped portion to be advanced into a patient's body and vasculature with relative ease and injury to surrounding tissue. And, because the guide wire does not extend through at least the 3-D shaped portion of the catheter, the size and outer diameter of that portion of the catheter need not be increased to accommodate the guide wire.

In a detailed embodiment, the 3-D shape is a helix wherein the helix is adapted to coil around the guide wire. In a neutral state, the helix has an expanded radius and a contracted axial length. When subjected to an external force, for example, a tensile force which longitudinally stretches the helix, the helix transits to a deformed state with a contracted radius and an expanded axial length, which provides the 3-D shaped portion of the catheter with a less traumatic profile for advancement in the patient's body. The catheter of the present invention advantageously allows the 3-D shaped portion to transit between the neutral and deformed states without interference from or with the guide wire.

In a more detailed embodiment, the tubular member has at least one lumen adapted to receive the guide wire through the proximal portion and the distal tip section. The at least one lumen has a first port in the proximal portion of the tubular member and a second port in the distal tip section, wherein one of the ports is adapted to allow the guide wire to exit the at least one lumen to outside the tubular member and the other of the ports is adapted to allow the guide wire to enter the at least one lumen from outside the tubular member.

In another more detailed embodiment, the proximal portion of the tubular member has at least a first band providing a first outer side tunnel and the distal tip section has at least a second band providing a second outer side tunnel, wherein each of the outer side tunnels is adapted to receive the guide wire therethrough.

The catheter may have additional lumens, for example, one lumen for an elongated support member preformed with the 3-D shape to support the 3-D shaped portion of the tubular member, and another lumen for electrode lead wires or any other components that extend through the tubular member.

BRIEF DESCRIPTION OF THE DRAWINGS

These and other features and advantages of the present invention will be better understood by reference to the following detailed description when considered in conjunction with the accompanying drawings wherein:

FIG. 2 is a top plan view of a 3-D shaped portion of the tubular member of the catheter of FIG. 1.

FIG. 2A is an end cross-sectional view of a tubular member of FIG. 2, taken along line A-A.

FIG. 6 is a top plan view of a 3-D shaped portion of a tubular member of a catheter in accordance with another embodiment of the present invention.

FIG. 6A is an end-cross-sectional view of the 3-D shaped portion of FIG. 6, taken along line A-A.

FIG. 6B is a side view of a distal tip end of the catheter of FIG. 6.

DETAILED DESCRIPTION OF THE INVENTION

Figure 1:
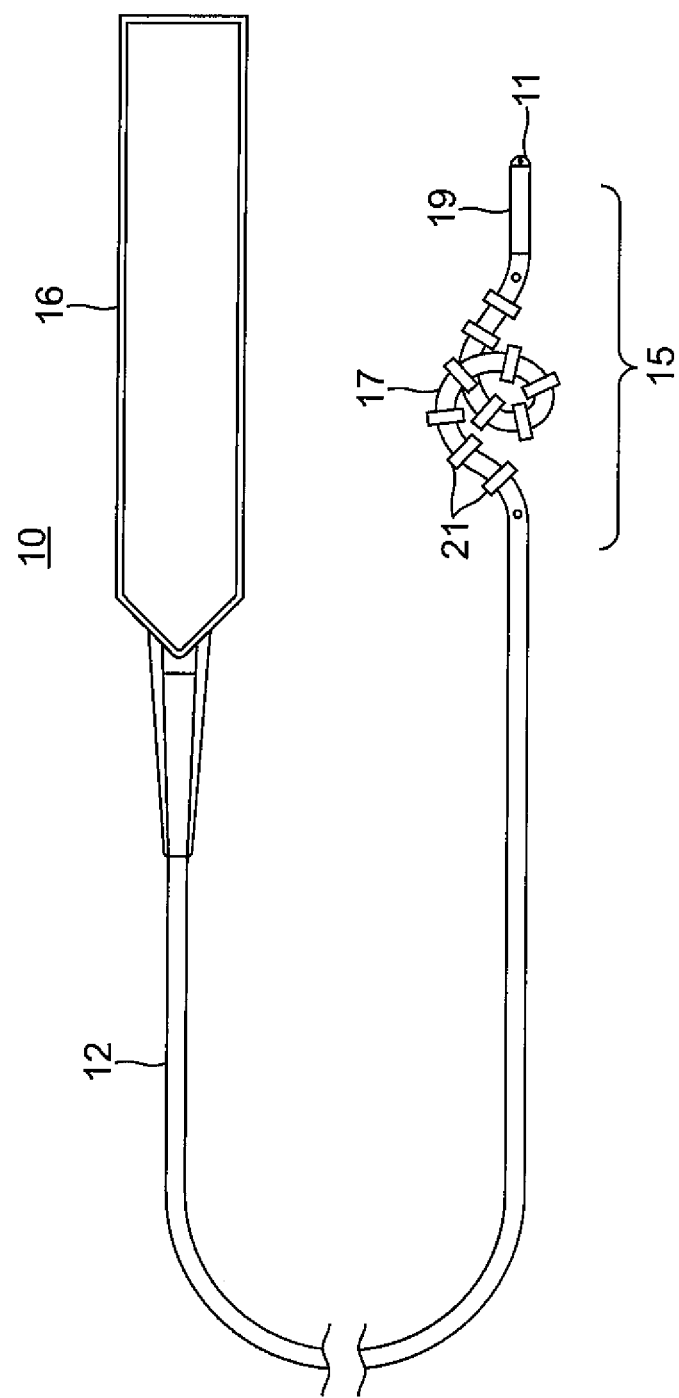
FIG. 1 is a top plan view of a catheter in accordance with an embodiment of the present invention.

With reference to FIG. 1, this invention shown and described herein relates to a catheter 10 having an elongated catheter body 12, a distal tip section 15 with a 3-D configuration, e.g., a 3-D portion 17 (for example, a helical configuration in the illustrated embodiment) with ring electrodes 21, and a control handle 16. In accordance with a feature of the present invention, the 3-D portion 17 is adapted for ablating an inner surface of a vessel or tubular region to block radial conduction lines without forming a closed loop line of block which may otherwise cause stenosis of the vessel or tubular region.

With reference to FIGS. 2 and 2A, the catheter body 12 and the 3-D portion 17 comprises an elongated tubular construction provided by a multi-lumened tubing 20 (preferably unbraided for at least the portion 17) with at least two lumens, one of which is dedicated to a guide wire 23. In the illustrated embodiment, there are three lumens 24, 25 and 26, where lumen 25 is dedicated to the guide wire 23. The catheter body 12 is flexible, i.e., bendable, but substantially non-compressible along its length. The catheter body can be of any suitable construction and made of any suitable material. A presently preferred construction, the tubing 20 is made of polyurethane or PEBAX and may comprise an imbedded braided mesh of stainless steel or the like to increase torsional stiffness of the catheter body so that, when the control handle 16 is rotated, the catheter body 12 will rotate in a corresponding manner.

The outer diameter of the catheter body is not critical, but is preferably no more than about 8 french, more preferably 5 french. The size of each lumen is not critical, provided the lumens can accommodate the respective components(s), including the guide wire 23, and for example, lead wires 40 for the ring electrodes 21 and an elongated support member 27 with shape memory to provide the 3-D configuration, such as the helical configuration of the portion 17 of the distal section 15. A preferred shape memory material is nitinol, which has excellent ductility, strength, corrosion resistance, electrical resistivity and temperature stability. A nitinol wire for use as the support member 27 has preferably a square cross-section (e.g., about 0.009 inch×0.009 inch) although the cross-section may also be circular or rectangular (e.g., with a width or diameter between about 0.006 inch and 0.012 inch). In one embodiment, the nitinol wire is preformed with a helical shape having a diameter of about 10 mm.

The ring electrodes 21 are carried on an outer surface of the tubing 20 on the 3-D portion 17 of the distal section 15. The lead wires 40 extend from the control handle 16, through the catheter body 12 and the helical proximal portion via the lumen 26. One method for attaching a lead wire 40 to a ring electrode 21 involves first making a small hole 30 (see FIG. 2) in and through a side wall of the tubing 20. Such a hole can be created, for example, by laser drilling or inserting a needle through the tubing 20 and heating the needle sufficiently to form a permanent hole. The lead wire 40 is then drawn through the hole by using a microhook or the like. The end of the lead wire 40 is then stripped of any coating and welded to the underside of the ring electrode 21, which is then slid into position over the hole and fixed in place with polyurethane glue or the like. Alternatively, each ring electrode 21 may be formed by wrapping the lead wire 40 around the outer surface of tubing 20 a number of times and stripping the lead wire of its own non-conductive coating on its outwardly facing surfaces. In such an instance, the lead wire 40 functions as a ring electrode. The plurality of ring electrodes ranges between about 5 to 12, and more preferably about 8 to 10.

The support member 27 extends from the control handle 16 to the distal section 15. However, it is understood that the support member 27 may have its proximal end at other locations throughout the catheter body 12. In one embodiment, the proximal end is located in the catheter body 12 about 25 mm proximal of the 3-D portion 17.

The support member 27 is preshaped with a 3-D configuration which is imparted to the tubing 20, including the portion spanning the 3-D portion 17. The support member has shape memory so that such that it elastically holds the 3-D configuration (or any other preformed shape) when no external forces are applied, assumes another or deformed shape when an external force is applied, and returns to the preformed shape when the external force is removed. In the illustrated embodiment, the support member 27 has a helical distal portion which 3-D configuration is imparted to the portion 17. Because of the shape memory of the support member 27, the helical portion 17 is elongated and straightened upon application of an external force (e.g., a tensile force and/or a compression force), and rebounds to its initial shape when the external force is removed. A distal end of the support member 27 is potted and anchored at the distal end of the tubing 20 in the lumen 24 by a plug 36 of adhesive, sealant or glue, such as epoxy, as shown in FIGS. 3 and 3A.

The dedicated lumen 23 for the guide wire 23 extends the entire length of the tubing 20. However, when the catheter is used with the guide wire 23, the lumen 23 is occupied by the guide wire 23 only in the catheter body 12 and at or near the distal end of the tubing 20. As shown in FIGS. 2 and 3, proximal exit port 38 and distal entry port 39 are formed in and through the side wall of the lumen 23 in the tubing 20 immediately proximal and immediately distal of the helical portion 17. As such, the guide wire 23 can be received in the lumen 23 throughout the catheter body 12, exit the lumen 23 and the catheter at exit port 38 to bypass the helical portion 17 and re-enter the lumen 23 at entry port 39.

Figure 3A:
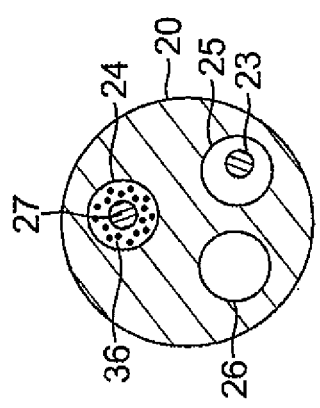
FIG. 3A is an end cross-sectional view of the distal section of FIG. 3, taken along line A-A.
Figure 3:
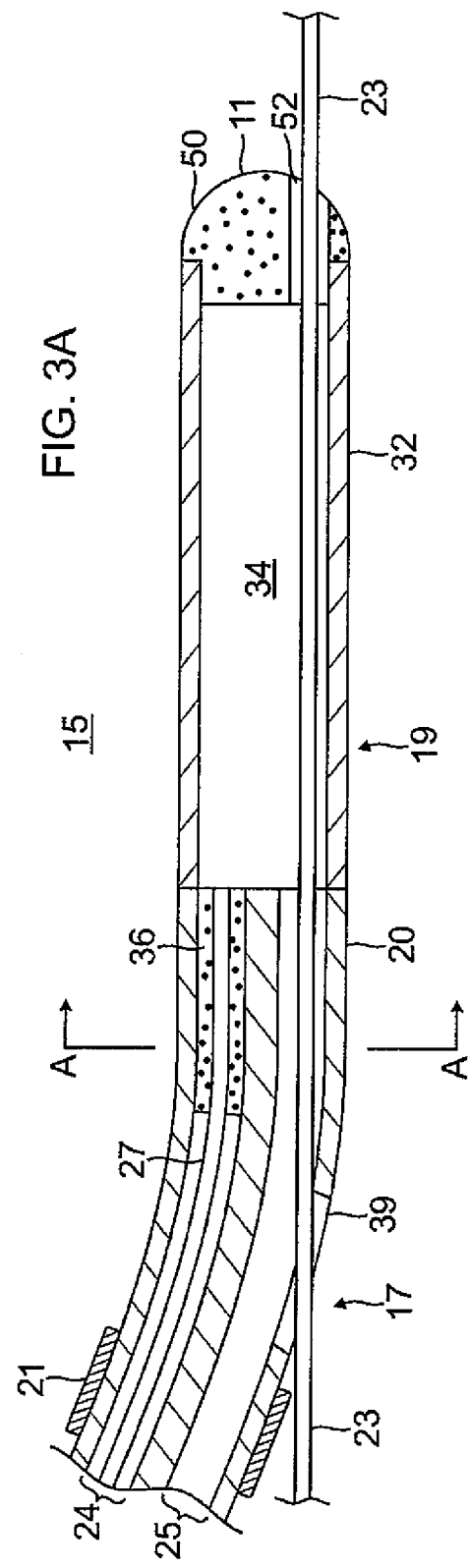
FIG. 3 is a side cross-sectional view of a distal section of the catheter of FIG. 1.

As also shown in FIGS. 3 and 3A, the generally straight distal portion 19 of the distal section 15 includes a short section of a single lumened tubing 32 whose proximal end is attached to a distal end of the multi-lumened tubing 20 of the helical portion 17. A central lumen 34 of the tubing 32 is generally sealed at its distal end by a dome plug 50 of sealant or glue, such as epoxy, except for an axial distal tip exit port 52 for the guide wire 23 to exit the catheter at the distal tip end. It is understood that the distal end of the support member 27 may extend into the dome plug 50 and anchored therein. It is also understood that the distal tip section need not have the generally straight distal portion 19 and that the dome plug 50 may be positioned at the distal end of the helical portion 17.

Figure 4:
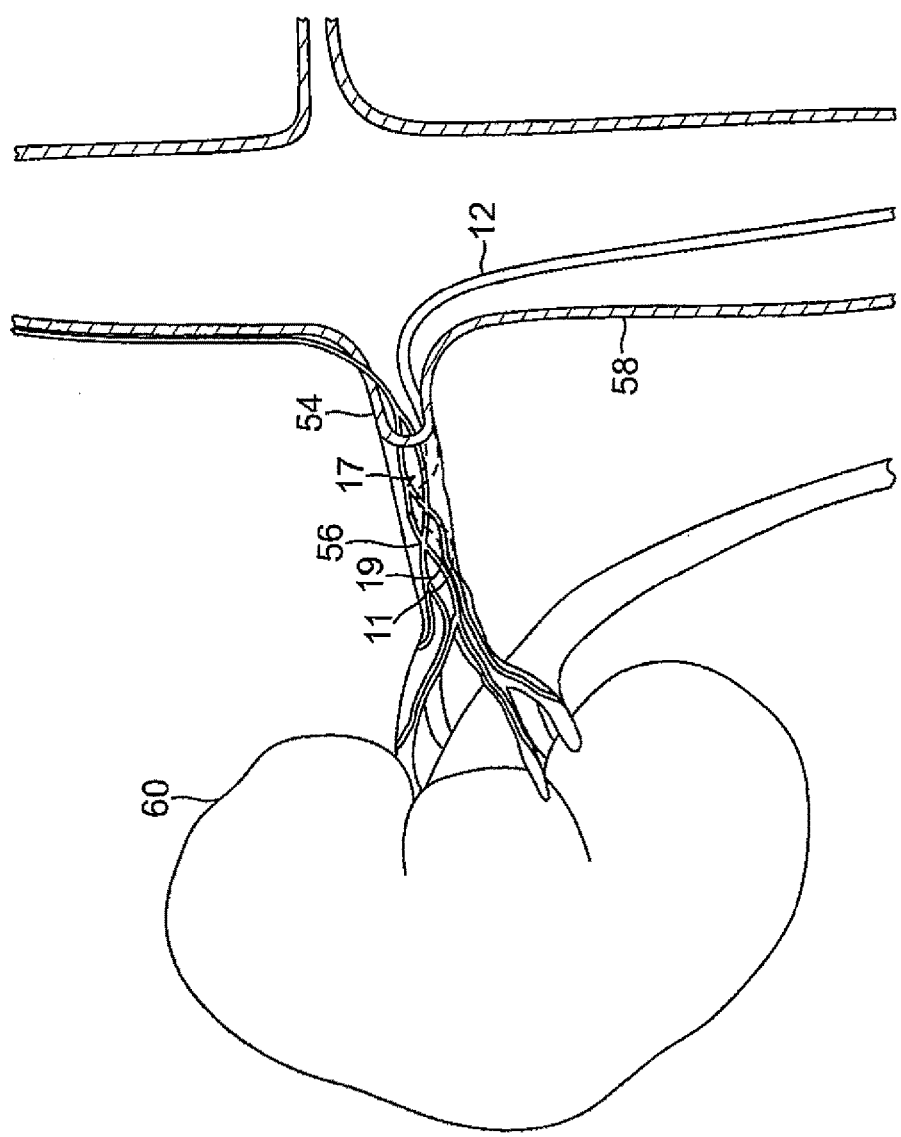
FIG. 4 is a schematic pictorial of a catheter of the present invention positioned in a renal artery.

FIG. 4 illustrates vessels or tubular regions in a patient's body, namely, aorta 58, and renal artery 54 extending into kidney 60. Accessed via the aorta 58, the renal artery 54 is a target site for renal denervation by means of catheter ablation. Prior to the catheter entering the patient's body and vasculature, the guide wire 23 is inserted into the catheter 10 distally from the control handle 16 and into the catheter body 12, as shown in FIG. 1, so that the catheter can move on and over the guide wire and be guided by the guide wire which precedes the catheter through the patient's vasculature. As shown in FIG. 2A, the guide wire travels through the lumen 23 through the entirety of the catheter body 12. The guide wire bypasses the helical portion 17 by exiting via the proximal port 38 proximal of the 3-D portion 17 and reentering the catheter via the distal port 39 distal of the helical portion. Because the guide wire is outside the helical portion 17, the helical portion 17 is unconstrained and free of external forces that would prevent it from assuming the 3-D configuration imparted by the support member 27.

Figure 5A:
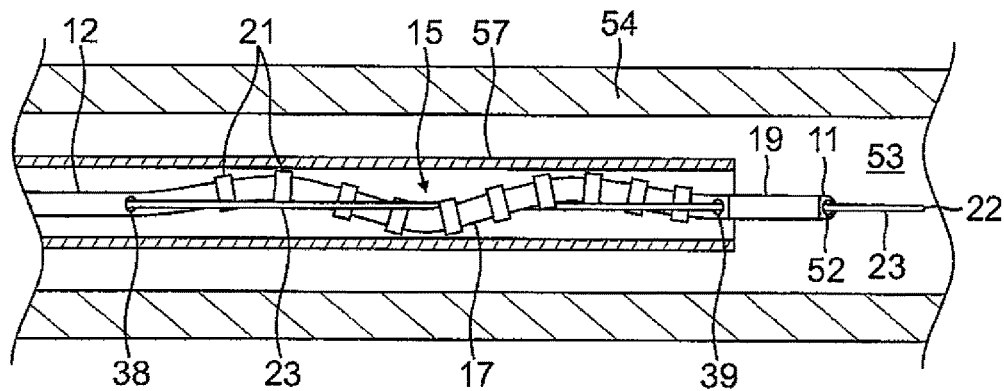
FIG. 5A is a side cross-sectional view of a catheter of the present invention in a vessel or tubular region prior to deployment.

Using standard guide wire procedures, or as the catheter enters the patient's body and vascular, preceded by the guide wire 23 which may be used with a guiding sheath 57, as shown in FIG. 5A, a distal tip end of the catheter (as formed by the dome plug 50) is advanced into the vascular, followed by the generally straight distal section 19. The generally straight distal portion 19 facilitates entry of the catheter into the patient's body and vascular. Before the 3-D portion 17 enters the patient's body, it is elongated in the axial direction and contracted in the radial direction by the application of an external tensile force in the proximal direction relative to the guide wire so that the 3-D portion 17 presents a less traumatic/more atraumatic profile as shown in FIG. 5A. As such, the 3-D portion 17 is more maneuverable for advancement in the vascular and the catheter is advantageously usable with a guide wire without requiring a larger outer diameter in the 3-D portion to accommodate the guide wire.

Figure 5B:
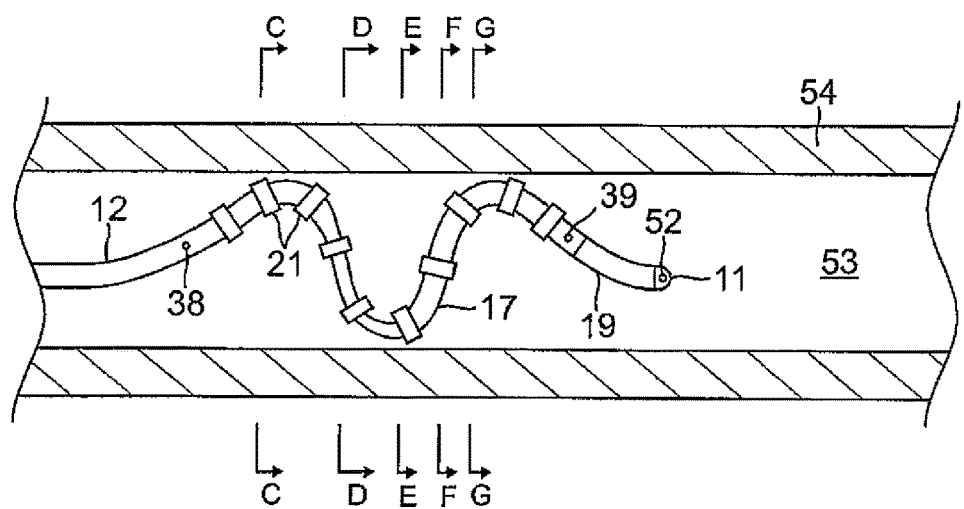
FIG. 5B is a side cross-sectional view of the catheter of FIG. 5A after deployment.
Figure 5C:
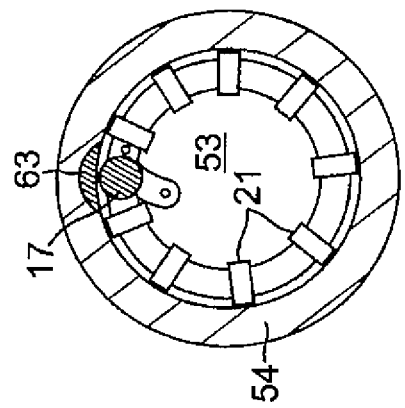
FIG. 5C is an end-cross-sectional view of the catheter of FIG. 5B, taken along line C-C.
Figure 5D:
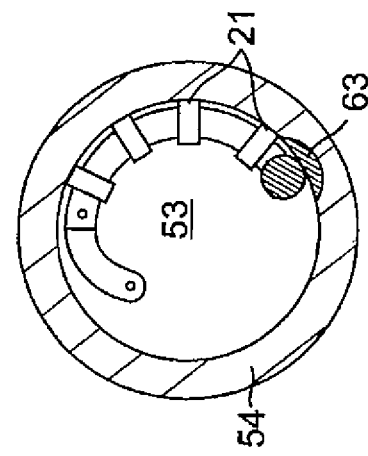
FIG. 5D is an end-cross-sectional view of the catheter of FIG. 5B, taken along line D-D.
Figure 5E:
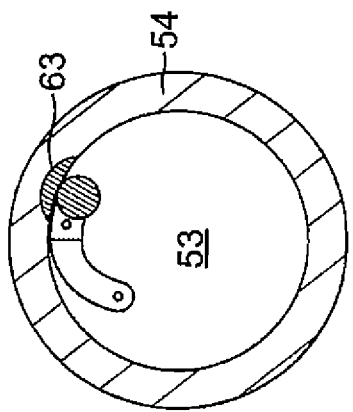
FIG. 5E is an end-cross-sectional view of the catheter of FIG. 5B, taken along line E-E.
Figure 5F:
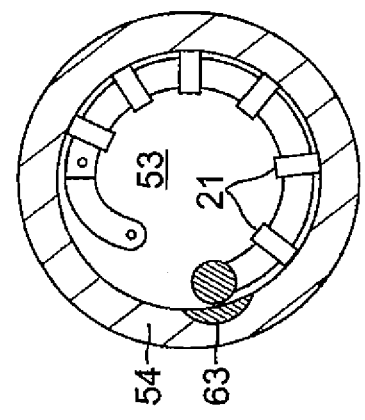
FIG. 5F is an end-cross-sectional view of the catheter of FIG. 5B, taken along line F-F.
Figure 5G:
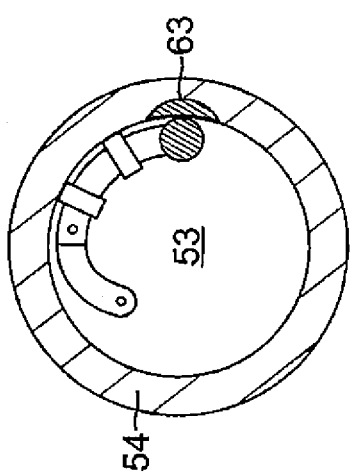
FIG. 5G is an end-cross-sectional view of the catheter of FIG. 5B, taken along line G-G.

At the treatment site with in lumen 53 of the vessel 54, the distal section 15 is deployed by being moved distally past the distal end of the guiding sheath 57. The guide wire 23 is then drawn proximally so that its distal end 22 slides back into the distal tip end port 52 and through the central lumen 34 of the generally straight portion 19. The distal end then exits the distal port 39 and back into the proximal port 38 and the lumen 25. Without being guided and constrained by the guide wire 23, the 3-D portion 17 reassumes its 3-D shape when deployed, for example, expanding in the radial direction and contracting in the axial direction to return to the helical configuration as shown in FIG. 5B, where the ring electrodes 21 come into contact with an inner circumferential surface of the vessel 54. As shown in FIGS. 5C-5G, the helical configuration enables each ring electrode 21 to contact a different radial location (for example, 360 degrees in FIG. 5C, 270 degrees in FIG. 5D, 135 degrees in FIG. E, 90 degrees in FIG. 5F, and 15 degrees in FIG. 5G) at a different depth along the vessel so that resulting lesions 63 terminate nerves and/or form a block around the vessel without creating a closed circumferential loop that could otherwise cause stenosis of the vessel. The shape memory support 27 advantageously allows the 3-D portion 17 to have a preformed shape, be deformed when subjected to an external force, and to reassume the preformed shape when the external force is removed. It is understood that where the 3-D configuration is a helical configuration as shown in the illustrated embodiment, the helical configuration can be coiled around the guide wire 23 such that the guide wire extends through a loop (or loops) 56 of the helical configuration (as shown in FIGS. 2A and 5A).

Figure 7A:
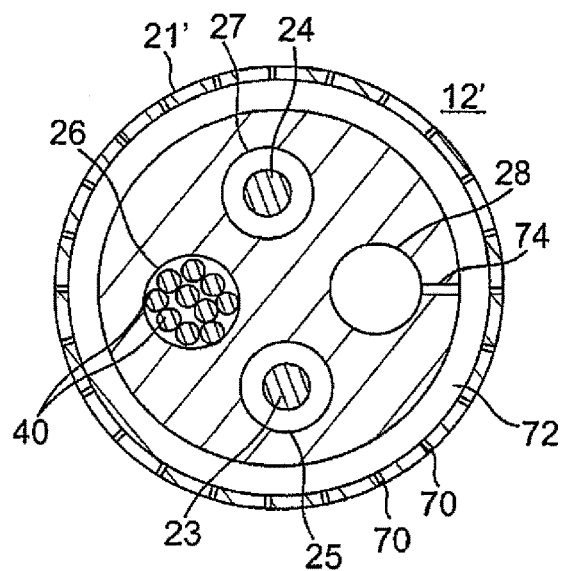
FIG. 7A is an end sectional view of the distal tip section of FIG. 7, taken alone line A-A.
Figure 7:
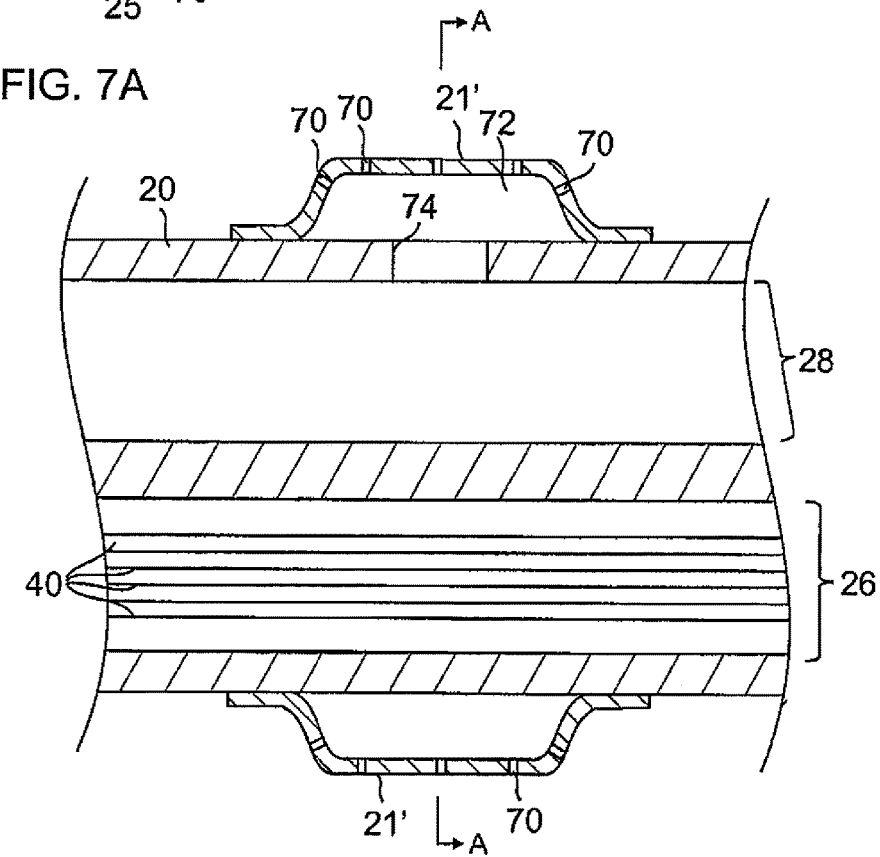
FIG. 7 is a side cross-sectional view of a distal tip section with irrigated ring electrodes, in accordance with another embodiment of the present invention.

FIGS. 7 and 7A illustrated a distal tip section 15 with at least one irrigated ring electrode 21' having a plurality of fluid ports 70. The irrigated ring electrode 21' has a raised profile such that an annular gap 72 is formed between the ring electrode 21' and an outer surface of tubing 20. Irrigation fluid is delivered to the ring electrode 21' via lumen 28 which may be fed at its proximal end by irrigation tubing (not shown) from the control handle 16. The fluid is passed from the lumen 28 to the annular gap via a passage 74 formed between the lumen and the irrigated ring electrode 21'. Fluid then passes to outside the ring electrode 21 via fluid ports 70 formed in the ring electrode.

In an alternate embodiment of the present invention, as shown in FIGS. 6 and 6A, a catheter 10' includes a plurality of band or rings 61 mounted on an outer surface of the tubing 20, each of which provides an outer side tunnel 62 to couple the catheter and the guide wire 23. The catheter 10' includes at least a proximal band or band 61P proximal of the 3-D portion 17 and at least a distal band 61D distal of the 3-D portion 17 to provide outer side tunnels 62P and 62D. The catheter 10' may also include a distal end band 61T (FIG. 6B) at or near the dome plug 50 at the distal tip end of the catheter to provide outer side tunnel 62T. In the illustrated embodiment, each band 61 has a circumference larger than the outer circumference of the tubings 20 and 32, wherein the excess circumference is pinched (and glued) to secure the ring onto the tubings 20 and 32 and form the side loop or tunnel through which the guide wire 23 is inserted. Extending from the catheter body 12 to the 3-D portion 17, the tubing 20 includes the lumen 24 for the support member 27 and the lumen 26 for the lead wires 40. However, there is no lumen for the guide wire 23 because the guide wire 23 extends outside of the catheter 20.

As the catheter 10' enters the patient's body and vascular, preceded by the guide wire which may be used with a guiding sheath 57, the 3-D portion 17 is similarly elongated in the axial direction and contracted in the radial direction by the application of an external tensile force in the proximal direction relative to the guide wire so that the 3-D portion 17 presents a less traumatic/more atraumatic profile. When the 3-D portion 17 reaches the treatment site, the portion 17 is moved beyond the distal end of the sheath 57 and the guide wire is drawn proximally relative to the catheter 10 until the distal tip end slides out of the distal end tunnel, the distal tunnel and then out of the proximal tunnel, whereupon the 3-D portion 17 shortens in the axial direction and expands in the radial direction to return to its original 3-D configuration. As with the catheter 10, the ring electrodes 21 of the catheter 10' come into contact with an inner surface 55 of the vessel 54. The helical configuration enables the ring electrodes 21 to contact a plurality of radial locations at different depths along the vessel so that resulting lesions form a block around the vessel without creating a closed loop that could otherwise cause stenosis of the vessel.

The ring electrodes 21 are constructed of a biocompatible metal, including a biocompatible metal alloy. A suitable biocompatible metal alloy includes an alloy selected from stainless steel alloys, noble metal alloys and/or combinations thereof. In another embodiment, the tip electrode is a shell is constructed of an alloy comprising about 80% palladium and about 20% platinum by weight. In an alternate embodiment, the shell is constructed of an alloy comprising about 90% platinum and about 10% iridium by weight. The rings may be uni-polar or bi-polar. In the illustrated embodiment, there are 10 ring electrodes forming five pairs of bi-polar ring electrodes. Each ring electrode is connected to a respective lead wire. The tip electrode is electrically connected to a source of ablation energy and/or an appropriate mapping or monitoring system by respective lead wires.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. In that regard, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. An ablation catheter configured for use with a removable guide wire, the removable guide wire being independent of the catheter, and the catheter comprising:
   an elongated tubular member having a proximal portion, a distal tip end portion, and an intermediate portion with a 3-D shape between the proximal portion and the distal tip end portion, the proximal portion being configured to extend in longitudinal alignment with the guide wire, and the intermediate portion being configured to extend around a portion of the removable guide wire that extends outside the tubular member, the elongated tubular member having at least first and second lumens extending through at least the intermediate portion; and
   a distal tip end exit port configured to allow the removable guide wire to exit the catheter at a distal tip end of the distal tip end portion;
   the second lumen of the tubular member extending through the proximal portion of the tubular member and the distal tip end portion of the tubular member, the second lumen having a first port in the proximal portion of the tubular member, and a second port in the distal tip end portion of the tubular member, wherein one of the first or second ports is configured to allow the removable guide wire to exit the second lumen to outside the tubular member and the other of the first or second ports is configured to allow the removable guide wire to enter the second lumen from outside the tubular member.

2. The catheter of claim 1, wherein the intermediate portion with the 3-D shape includes a helical configuration.

3. The catheter of claim 2, wherein the helical configuration is configured to elongate axially and contract radially in a neutral state and to shorten axially and expand radially when subjected to a tensile force.

4. The catheter of claim 2, wherein the helical configuration is configured to contact a plurality of radial locations on an inner surface of a vessel at different depths along the vessel.

5. The catheter of claim 1, further comprising at least one ring electrode mounted on the intermediate portion with the 3-D shape.

6. The catheter of claim 5, wherein the at least one ring electrode is adapted for ablation.

7. The catheter of claim 5, further comprising:
   at least one lead wire for the at least one ring electrode, and
   a third lumen in the elongated tubular member, the at least one lead wire extending through the third lumen.

8. The catheter of claim 1, further comprising an elongated support member with shape memory extending through the first lumen of the elongated tubular member to impart the 3-D shape to the intermediate portion with the 3-D shape.

9. An ablation catheter configured for use with a removable guide wire that is independent of the catheter, and the catheter comprising:
an elongated tubular member having at least a first lumen and a second lumen extending therethrough, the elongated tubular member having an intermediate portion with a 3-D shape configured to coil around a portion of the removable guide wire that extends outside the tubular member, a distal tip end portion, and a first portion proximal of the intermediate portion, the first portion being configured to extend in longitudinal alignment with the tubular member; and
a distal tip end exit port configured to allow the removable guide wire to exit the catheter at a distal tip end of the distal tip end portion,
the second lumen in the tubular member comprising:
a proximal portion extending through the first portion of the tubular member, the proximal portion of the second lumen having a first port, and
a distal portion extending through the distal tip end portion of the tubular member, the distal portion of the second lumen having a second port,
the proximal and distal portions of the second lumen being configured to allow the removable guide wire to exit the proximal portion of the second lumen through the first port to outside the tubular member, and to enter the distal portion of the second lumen through the second port from outside the tubular member.

10. The catheter of claim 9, wherein the intermediate portion with the 3-D shape includes a helical configuration.

11. The catheter of claim 10, wherein the helical configuration is configured to elongate axially and contract radially in a neutral state and to shorten axially and expand radially when subjected to a tensile force.

12. The catheter of claim 10, wherein the helical configuration is configured to contact a plurality of radial locations on an inner surface of a vessel at different depths along the vessel.

13. The catheter of claim 9, further comprising at least one ring electrode mounted on the intermediate portion with the 3-D shape.

14. The catheter of claim 13, further comprising:
at least one lead wire for the at least one ring electrode, and
a lead wire lumen in the elongated catheter body, the at least one lead wire extending through the lead wire lumen.

15. The catheter of claim 13, wherein the at least one ring electrode is adapted for ablation.

16. The catheter of claim 9, further comprising an elongated support member with shape memory extending through a third lumen in the elongated tubular member to impart the 3-D shape to the intermediate portion with the 3-D shape.

17. An ablation catheter adapted for use with a removable guide wire that is independent of the catheter, the catheter comprising:
an elongated tubular member having a proximal portion, a distal tip end portion, and an intermediate portion with a 3-D shape between the proximal portion and the distal tip end portion, the elongated tubular member having at least first and second lumens extending through at least the intermediate portion; and
a distal tip end exit port configured to allow the removable guide wire to exit the catheter at the distal tip end of the distal tip end portion,
the proximal portion being configured to extend in longitudinal alignment with the guide wire and comprising a proximal portion exit port configured to allow the removable guide wire to exit the proximal portion of the tubular member,
the intermediate portion being configured to extend around a portion of the removable guide wire that extends out the proximal portion exit port to outside the tubular member, and
the distal tip end portion comprising a distal tip end portion entrance port configured to allow the removable guide wire to enter the distal tip end portion from outside of the tubular member.

18. The catheter of claim 17, wherein the intermediate portion with the 3-D shape includes a helical configuration.

19. The catheter of claim 18, wherein the helical configuration is configured to elongate axially and contract radially in a neutral state and to shorten axially and expand radially when subjected to a tensile force.

20. The catheter of claim 18, wherein the helical configuration is configured to contact a plurality of radial locations on an inner surface of a vessel at different depths along the vessel.

* * * * *